United States Patent [19]
Streck et al.

[11] Patent Number: 5,336,200
[45] Date of Patent: Aug. 9, 1994

[54] RETRACTABLE SLEEVE-PROTECTION FOR INJECTION APPARATUS EMPLOYING CARPULES

[75] Inventors: Donald A. Streck, Kailua, Hi.; Thomas C. Kuracina, Ojai; Randall E. Ohnemus, Ventura, both of Calif.

[73] Assignee: InjectiMed, Inc., Ventura, Calif.

[21] Appl. No.: 850,376

[22] Filed: Mar. 10, 1992

[51] Int. Cl.$^5$ .............................................. A61M 5/32
[52] U.S. Cl. ..................................... 604/198; 604/89; 604/232
[58] Field of Search ............... 604/198, 110, 263, 192, 604/82, 86, 89, 87, 88, 232

[56] References Cited

U.S. PATENT DOCUMENTS

| | | | |
|---|---|---|---|
| 2,157,503 | 5/1939 | Smith | 604/89 |
| 3,080,866 | 3/1963 | Friedman | 604/88 |
| 3,511,239 | 5/1970 | Tuschhoff | 604/89 |
| 4,695,274 | 9/1987 | Fox | 604/198 |
| 4,826,489 | 5/1989 | Haber et al. | 604/195 |

FOREIGN PATENT DOCUMENTS 2202747 10/1988 United Kingdom.

*Primary Examiner*—C. Fred Rosenbaum
*Assistant Examiner*—Vanitha Alexander
*Attorney, Agent, or Firm*—Donald A. Streck

[57] ABSTRACT

This invention is a carpule-using syringe assembly having a needle protected to minimize the chance of accidental needle-stick. There is a carpule having a pierceable end and a syringe body for receiving and holding the carpule with the pierceable end adjacent an opening in an end portion of the syringe body. A cap is disposed over the pierceable end. The cap includes a support portion disposed in the opening. There are carpule-piercing portions for piercing the pierceable end of the carpule through the cap and a needle having a patient-piercing end. A retractable protective sleeve formed of a plurality of longitudinal slats is disposed over the patient-piercing end of the needle. Finally, there is provision for attaching the needle and the retractable protective sleeve in combination to the support portion with the needle in communication with an interior portion of the carpule through the carpule-piercing portions.

4 Claims, 7 Drawing Sheets

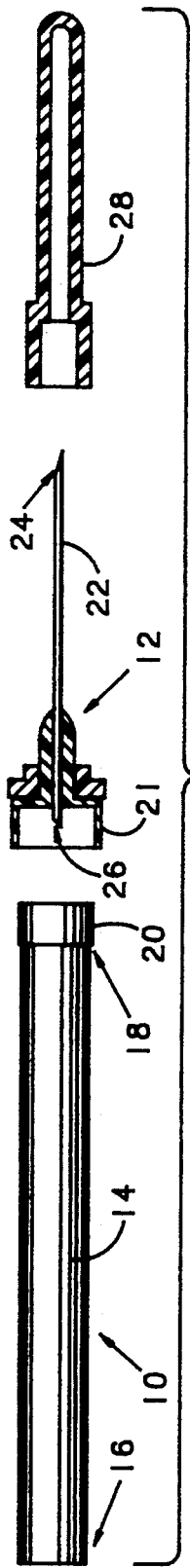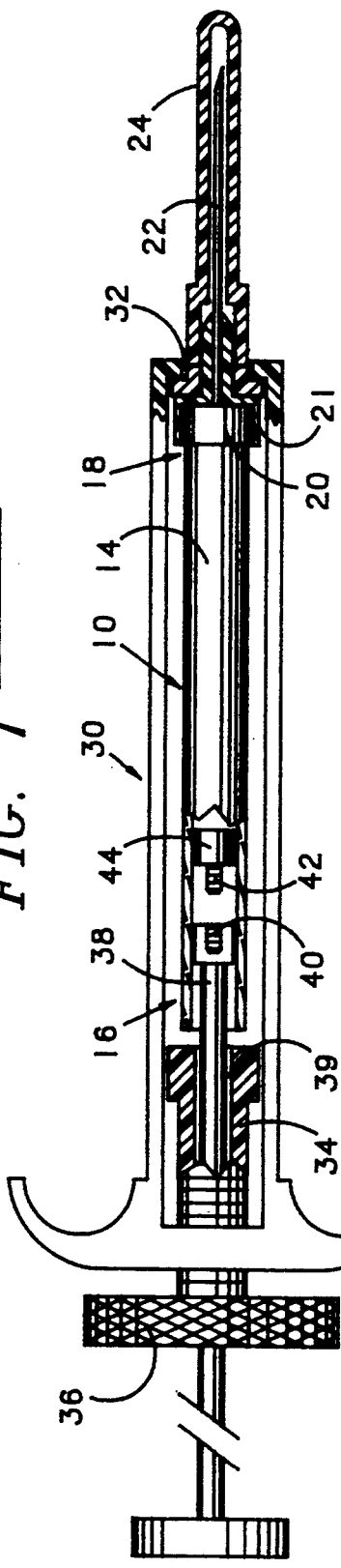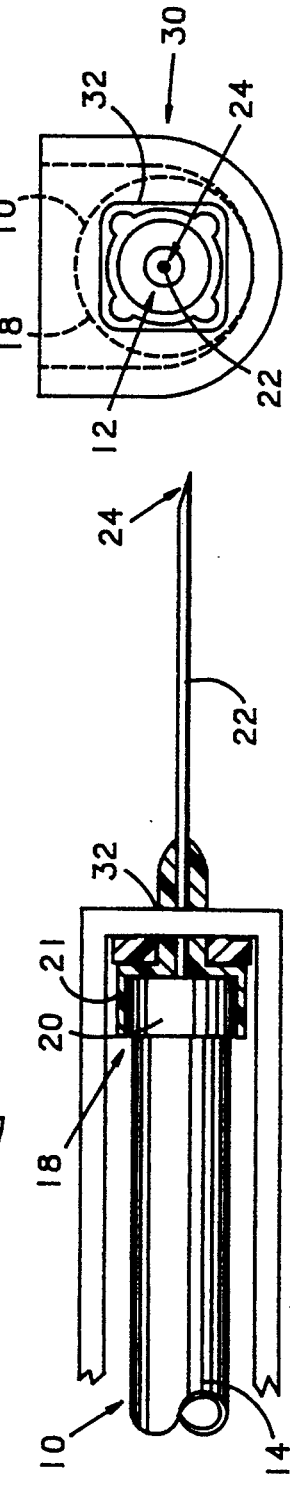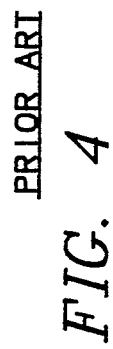
FIG. 1 PRIOR ART
FIG. 2 PRIOR ART
FIG. 3 PRIOR ART
FIG. 4 PRIOR ART

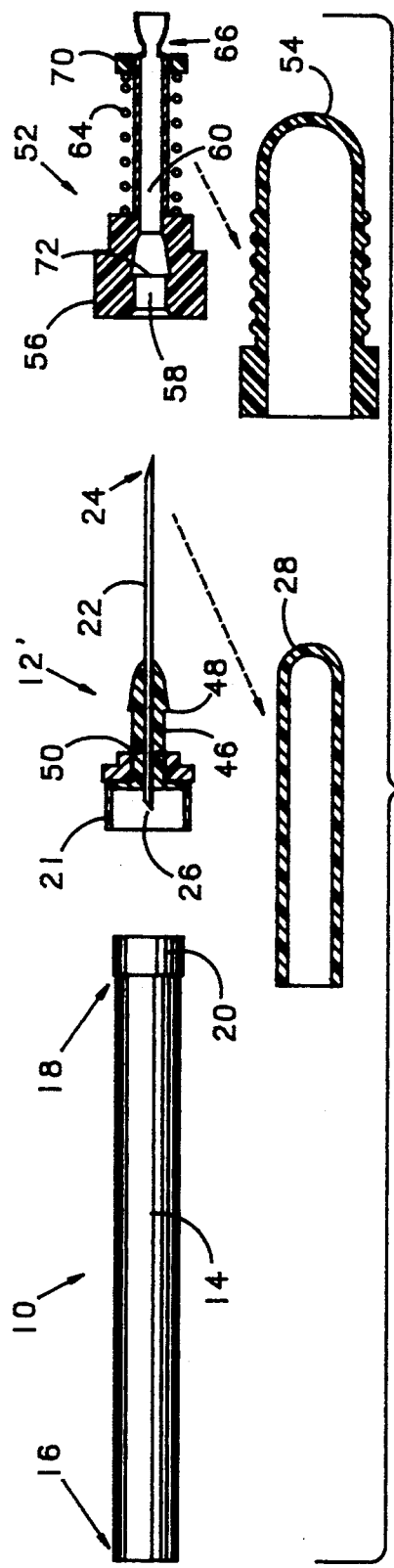
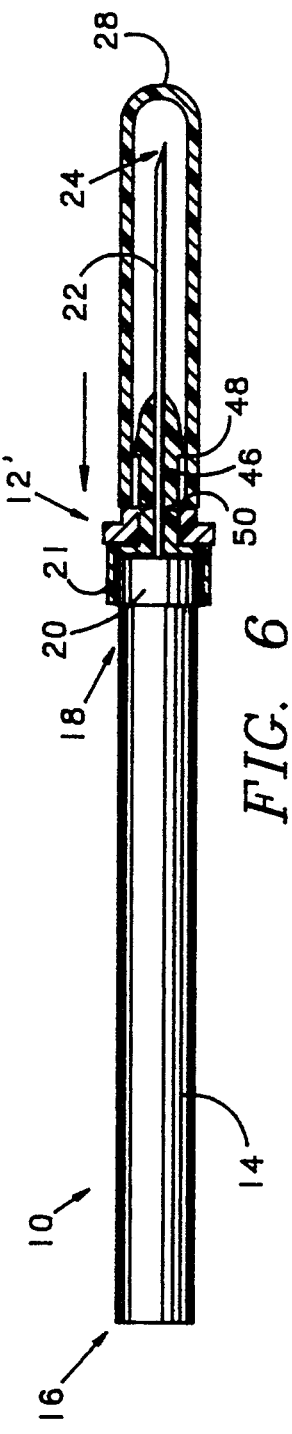
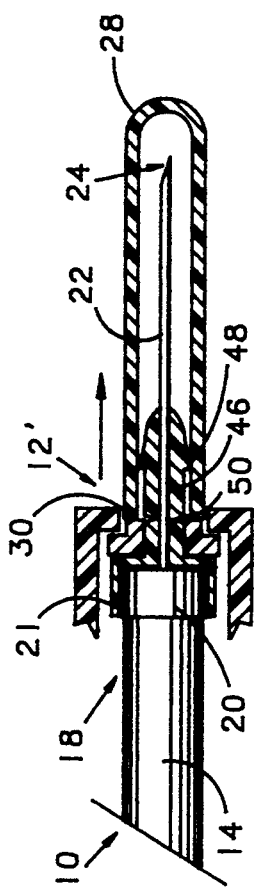
FIG. 5
FIG. 6
FIG. 7

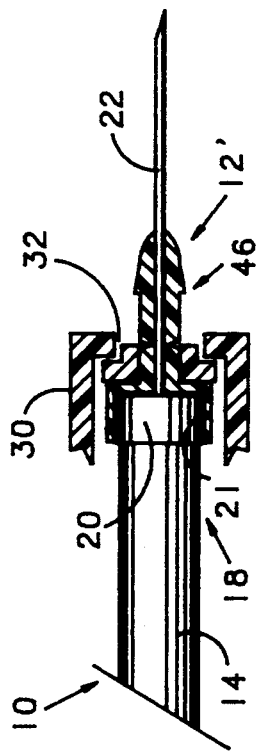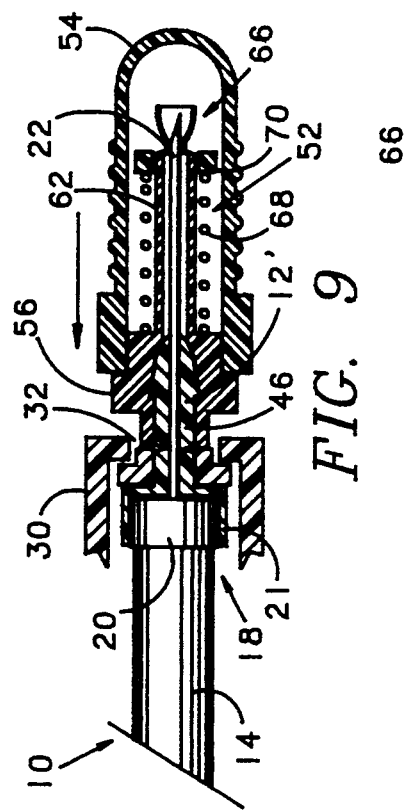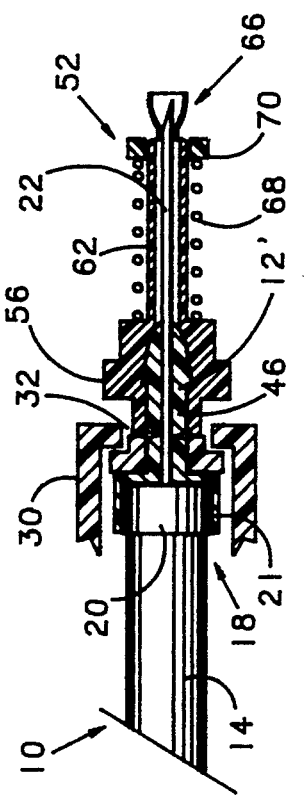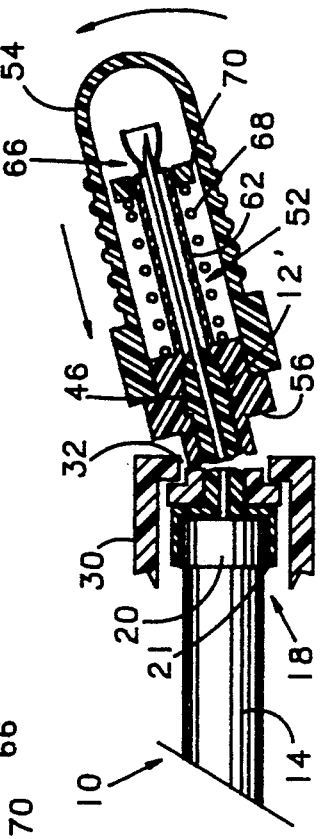
FIG. 8
FIG. 9
FIG. 10
FIG. 11

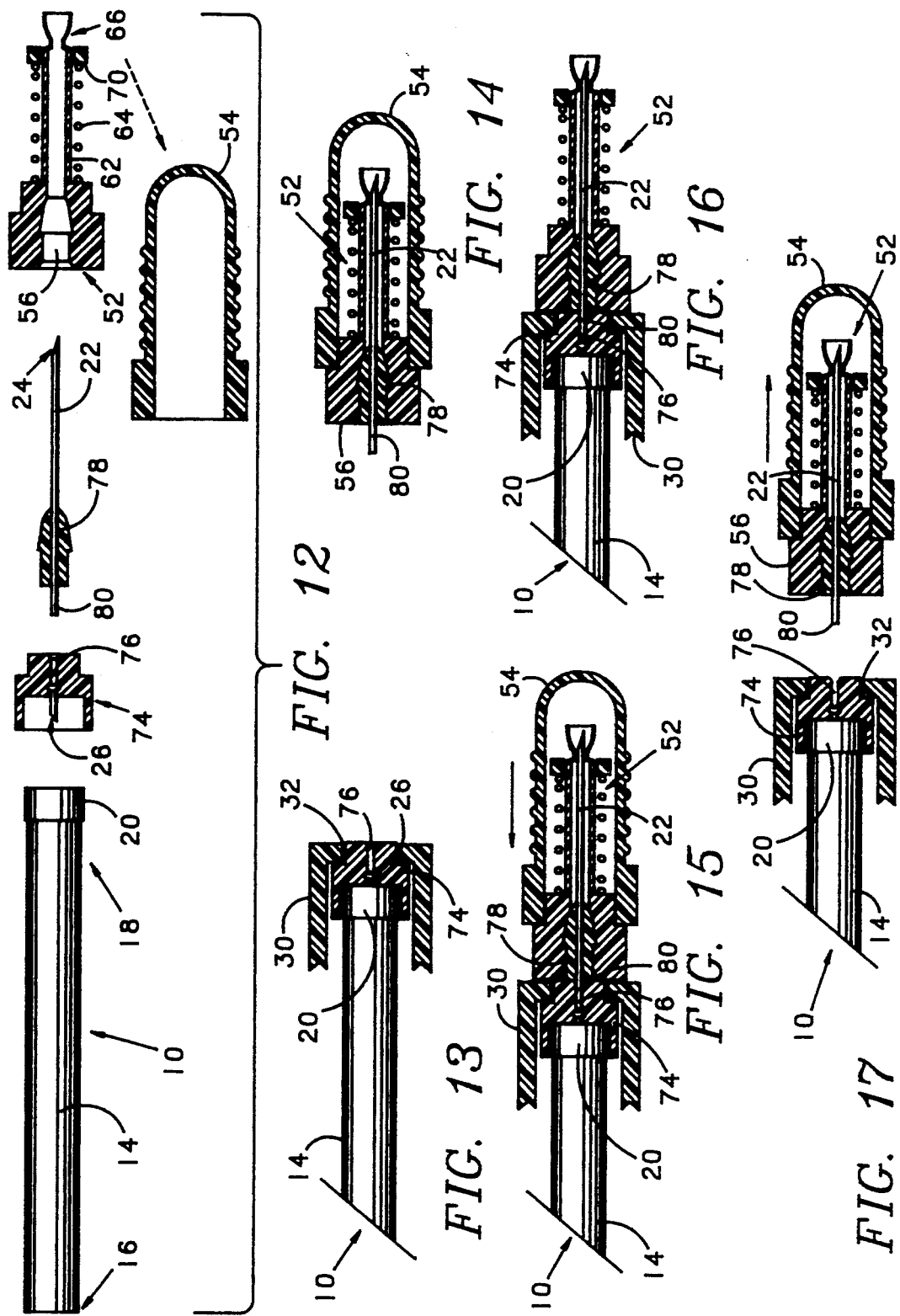

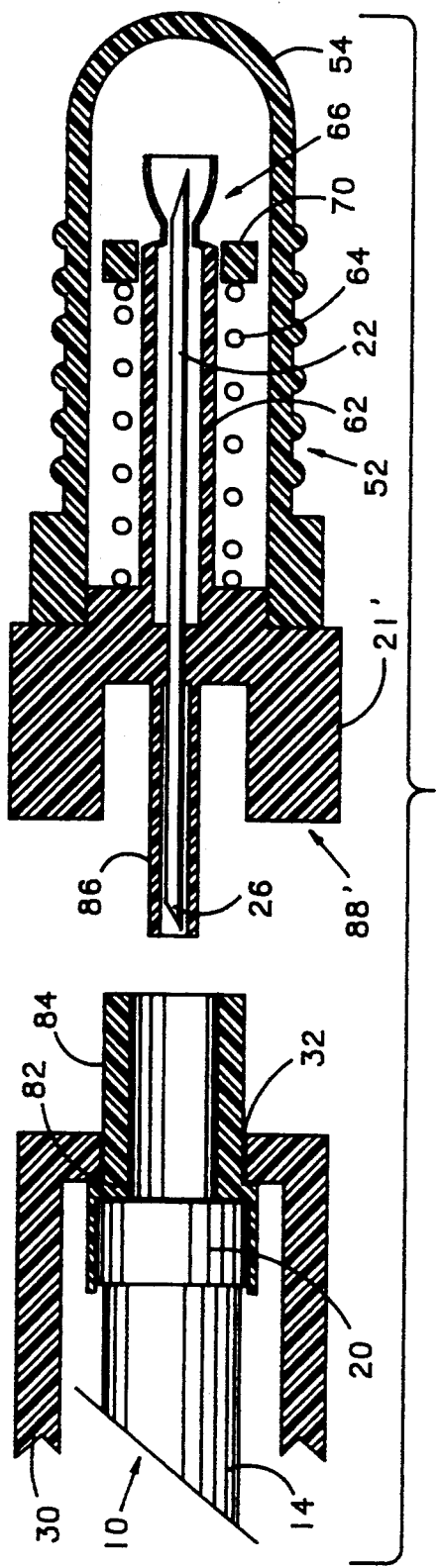
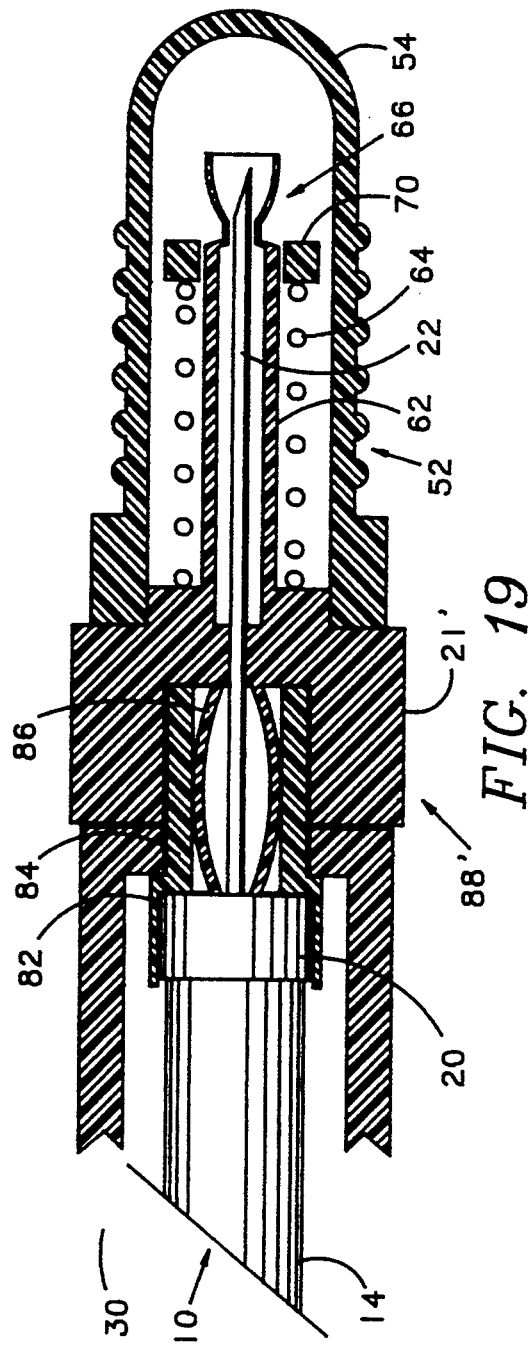

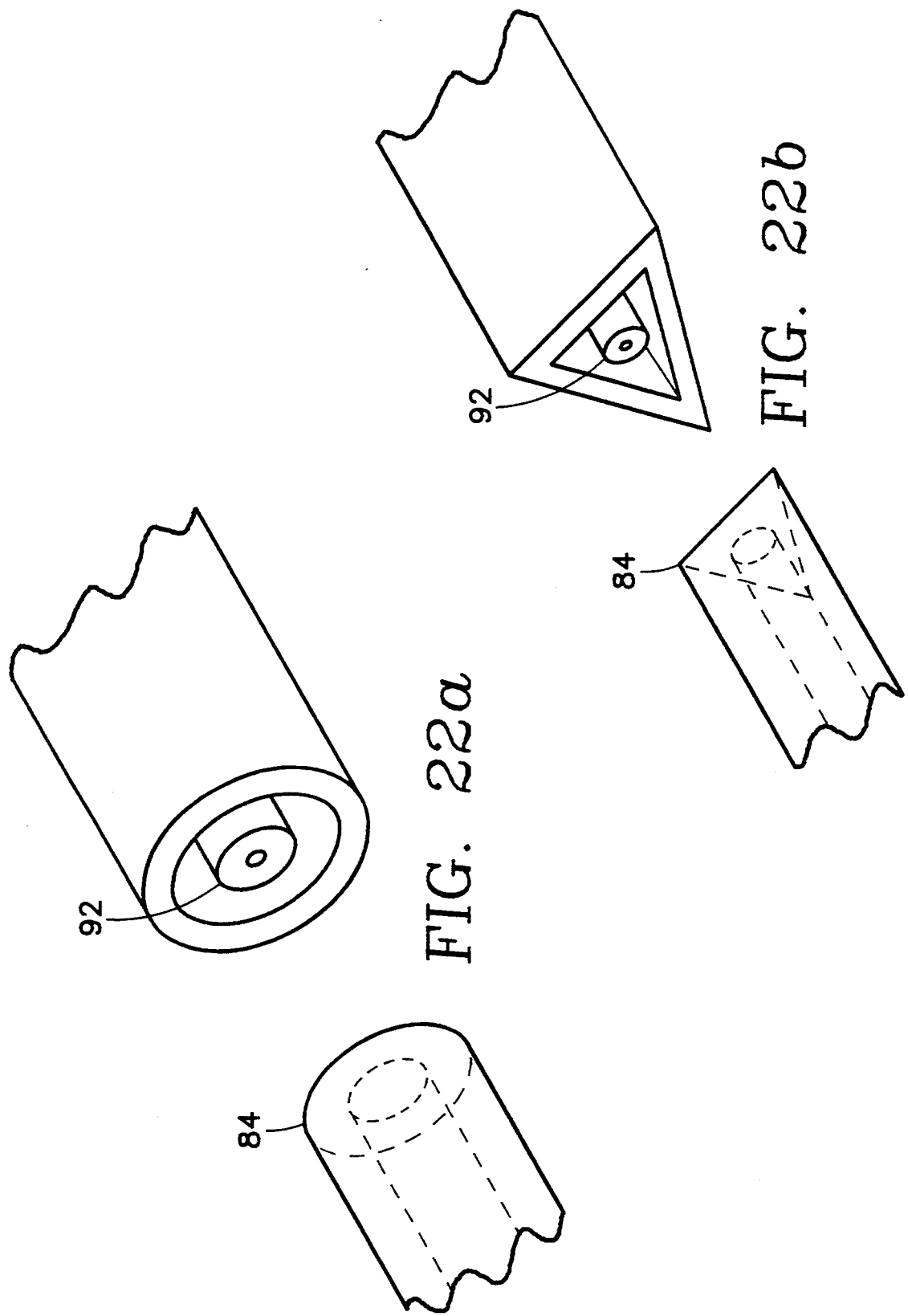

RETRACTABLE SLEEVE-PROTECTION FOR INJECTION APPARATUS EMPLOYING CARPULES

BACKGROUND OF THE INVENTION:

This invention relates to medical devices for injecting living bodies and, more particularly, to safety features incorporated therewith. In particular, it relates to a carpule-using syringe assembly having a needle protected to minimize the chance of accidental needle-stick.

In U.S. Pat. No. 4,998,922 by Thomas C. Kuracina entitled SAFETY SYRINGE CAP MINIMIZING NEEDLE-STICK PROBABILITY which issued Mar. 12, 1991, a safety device for hypodermic needles and the like is shown. The inventions shown hereinafter are improvements thereto by inventors including and/or working with Mr. Kuracina. In the interest of simplicity herein, the teachings of that patent are incorporated herein by reference and the discussion of the background art will be kept to a minimum.

A typical prior art hypodermic syringe includes a barrel having a moving plunger therein. A needle having a sharp beveled tip extends from the end opposite the end of the barrel into which the plunger is inserted. The needle is covered by a removeable cap for safety purposes. The problem to be solved and avoided is the accidental sticking of users of the syringe by the tip after use where the tip may carry body fluids containing agents of hepatitis B, AIDS, and the like. Accidental needle stick is a very common problem in the health care industry and besides the risk of serious illness or even death as a result thereof, the insurance industry spends over a billion dollars a year in the testing of individuals who have been subjected to post-use needle stick.

The 1979 patent of Alvarez proposed a retractable plastic protective sleeve over the needle. The Alvarez sleeve has an inner hub which fits around the base of the needle and an outer hub through which the tip of the needle passes. The inner and outer hubs are connected by curved slats. When the needle is to be inserted into the body of a patient, the force required to move the sleeve from its extended position to its retracted position can be depicted as a straight line beginning with very little required force to initiate movement. Thus, there is really no actual safety from a large variety of ways in which accidental needle stick takes place. Even if the sleeve fully extends after use, a slight blow against a user or observer in the area will cause the sleeve to retract and the tip to stick the unfortunate person.

With respect to the action of the basic protective sleeve of the above-referenced Kuracina patent by comparison, a high degree of force is required to move the protective sleeve from its extended position covering the tip. Moreover, a spring-biased locking collar is added over the protective sleeve which all but prevents the protective sleeve from moving from its extended position covering the tip. The collar must be moved from its locked position to a retracted, unlocked position before the unique deformation qualities of the sleeve take effect. After use, the locking collar springs back to its locked position. Thus, in virtually all "accidental" contact with the tip end of a hypodermic syringe, actual penetration by the tip should be prevented.

Carpule-based systems are known in the art. As shown in FIG. 1, the basic elements are a carpule 10 and a two-ended needle assembly 12. The carpule 10 comprises a cylinder 14 of plastic or glass having an open end 16 and a capped end 18. The capped end is closed by a piece of plastic or rubber (not shown) held in place by a collar 20. The two-ended needle assembly 12 comprises a cap 21 sized to fit over the collar 20. A needle 22 having an injection tip 24 on one end and a carpule-piercing tip 26 on the other end is concentrically held by the cap 21. As seen in FIG. 1, the carpule-piercing tip 26 extends to just within the cap 21 while the injection tip 24 is extended for use in its normal fashion. Typically, there is a plastic cover 28 which snugly fits over the injection tip 24 and the needle 22 up to the cap 21. The cover 28 protects the needle 22 and injection tip 24 as well as providing a safe way in which to handle the two-ended needle assembly 12.

In use, the two-ended needle assembly 12 is placed over the capped end 18 of the carpule 10 and the two in combination are disposed in the syringe assembly 30 of FIG. 2 with the cover 28 and needle 22 extending through a hole 32 provided therefor. The syringe assembly 30 has a pressure member 34 threaded through the rear thereof in concentric alignment with the open end 16 of the carpule 10. By turning the knob 36 to tighten the pressure member 34 against the open end 16 of the carpule 10, the carpule 10 is forced against the two-ended needle assembly 12 causing the carpule-piercing tip 26 to pierce the rubber or plastic to the interior of the carpule 10. A plunger rod 38 extends through a concentric bore 39 in the pressure member 34. The inner end of the plunger rod 38 has a threaded concentric bore 40 which mates with a threaded rod 42 extending concentrically backward toward the open end 16 from a plunger member 44 disposed within the carpule 10. By pushing the plunger rod 38 forward to contact the threaded rod 42 and turning it in a tightening direction, the plunger member 44 is temporarily attached to the end of the threaded rod 42. As thus configured, the syringe assembly 30 in combination with the carpule 10 and two-ended needle assembly 12 acts like a normal syringe and can be used to inject fluid contained in the carpule 10 or to withdraw fluids through the needle 22 into the carpule 10. Moreover, they can be used several times and can be disassembled and reassembled for further use.

With a conventional Kuracina type protective sleeve, it is delivered as part of an assembly containing the needle 22. Unfortunately, as depicted in FIGS. 3 and 4, the hole 32 in the end of the syringe assembly 30 is too small to accept the two-ended needle assembly 12 if a Kuracina type protective sleeve is attached thereto. Even in those syringe assemblies 30 where the hole 32 is in the form of a slot, the size is too small. Obviously, new syringe assemblies 30 could be manufactured for use with two-ended needle assemblies 12 having a Kuracina type protective sleeve attached thereto. The problem is one of being able to employ the large established base of syringe assemblies 30 in which the hole or slot 32 is too small.

In a co-pending application entitled MEDICAL INJECTION DEVICES WITH SAFETY FEATURES filed on even date herewith, certain improvements to the Kuracina protective sleeve are disclosed. The inventions described hereinafter are modifications to the above-described two-ended needle assemblies 12 and the manner of attaching a Kuracina protective sleeve in its various embodiments so as to allow the large established base of syringe assemblies 30 in which the hole or slot 32 is too small to be employed with protected needles.

The 1964 patent to Armao (3,134,380) shows a spring-loaded collapsible protective sleeve carried by a two-ended needle assembly used to attach a needle to a carpule and is, therefore, relevant to this invention.

Other objects and benefits of the inventions disclosed herein will become apparent from the detailed description which follows hereinafter when taken in conjunction with the drawing figures which accompany it.

SUMMARY:

The foregoing object has been achieved in a carpule-using syringe assembly wherein a syringe assembly carries a carpule for piercing by a needle also carried by the syringe assembly, by the improvement of the present invention for adding a protective sleeve to the needle comprising, a cap disposed over a pierceable end of the carpule, the cap having a support portion extending concentrically outward therefrom and extend beyond an outer end of the syringe assembly, the support portion having a longitudinal bore therethrough; and, a protected needle assembly carried by the support portion, the protected needle assembly including the needle with an inner portion disposed in the bore and a retractable protective sleeve disposed over an outer tip portion of the needle.

In a first embodiment, the needle is a two-ended needle carried by the support portion having a carpule-piercing end for piercing the carpule and a tipped end for use on a patient; and, the retractable protective sleeve is carried by a base member which has a socket which fits over the support portion. Additionally, the support portion and the base member include means for locking them together when the support portion is inserted into the socket; and, the support portion has a circumferential groove adjacent the cap forming a weak point at which the support portion and the needle can be broken off in combination with the retractable protective sleeve when use of the syringe assembly is completed.

In a second embodiment, the needle is in two parts with a carpule-piercing part extending from an inner portion of the bore into the cap and a patient piercing part carried in combination with the retractable protective sleeve; and, the retractable protective sleeve is carried by a base member also carrying the patient piercing part of the needle with a mounting portion of the needle extending into an outer portion of the bore to removably attach the patient piercing part of the needle in combination with the retractable protective sleeve to the support portion.

In a third embodiment, the retractable protective sleeve is carried by a base member which has a second bore which fits over the support portion; and, the needle is a two-ended needle carried by the base member concentrically disposed within the second bore having a carpule-piercing end for piercing the carpule and a tipped end for use on a patient. Preferably, there is also a retracting protective sleeve disposed over the carpule-piercing end of the needle. The retracting protective sleeve may comprise a plurality of longitudinal slats. Also, the second bore and the support portion may be non-cylindrical and of mating cross-sectional shapes having a pre-established relationship to a positional orientation of a patient-piercing tip of the needle whereby the positional orientation of the patient-piercing tip can be established when the syringe assembly is assembled with the carpule and the protected needle assembly.

In a fourth embodiment, the needle is in two parts comprising a carpule-piercing part and a patient piercing part; the bore comprises an inner bore adjacent the cap on one end carrying an inner portion of the carpule-piercing part and an outer bore of larger diameter than the inner bore on an opposite end concentrically extending over an outer portion of the carpule-piercing part; and, the retractable protective sleeve is carried by a base member also carrying the patient piercing part of the needle in a central bore therethrough, the base member having a projection extending therefrom containing a portion of the central bore not carrying the patient piercing part, the projection being sized and shaped to fit within the outer bore with the outer portion of the carpule-piercing part disposed the portion of the central bore not carrying the patient piercing part. Preferably, the projection is concentrically disposed in an outer bore of the base member sized and shaped to fit over the opposite end of the support portion. Also, mating portions of the cap and the protected needle assembly may be non-cylindrical and of mating cross-sectional shapes having a pre-established relationship to a positional orientation of a patient-piercing tip of the needle whereby the positional orientation of the patient-piercing tip can be established when the syringe assembly is assembled with the carpule and the protected needle assembly.

DESCRIPTION OF THE DRAWINGS:

FIG. 1 is a partially cutaway exploded drawing of the components of a prior art carpule approach to hypodermic syringes.

FIG. 2 is a partially cutaway, top view drawing of the components of FIG. 1 mounted in a prior art carpule-holding hypodermic syringe.

FIG. 3 is a partially cutaway, enlarged, top view drawing of the front portion of the carpule-holding hypodermic syringe of FIG. 2.

FIG. 4 is a front view drawing of FIG. 3.

FIG. 5 is a partially cutaway, exploded, plan view drawing of the components of a carpule approach to hypodermic syringes according to the present invention in a first embodiment.

FIGS. 6–11 depict the manner of assembly and use of the components of FIG. 5.

FIG. 12 is a partially cutaway, exploded, plan view drawing of the components of a carpule approach to hypodermic syringes according to the present invention in a second embodiment.

FIGS. 13–17 depict the manner of assembly and use of the components of FIG. 12.

FIG. 18 is a partially cutaway, enlarged, partially exploded plan view drawing of the components of a carpule approach to hypodermic syringes according to the present invention in a third embodiment.

FIG. 19 is a partially cutaway, enlarged, plan view drawing of the components of a carpule approach to hypodermic syringes according to the present invention in its third embodiment of FIG. 18 shown fully assembled for use.

FIG. 22a is a perspective view of cylindrical mating portions of the cap and protected needle assembly of FIGS. 20 and 21, and FIG. 22b is a perspective view of non-cylindrical mating portions of the cap and protected needle assembly of FIGS. 20 and 21.

Figure 20:
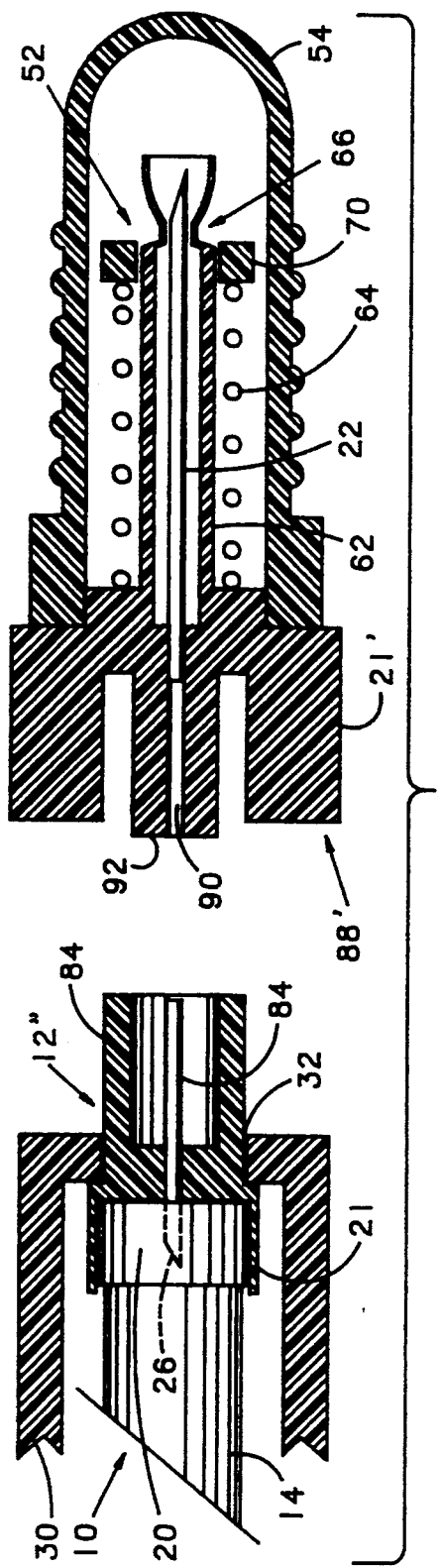
FIG. 20 is a partially cutaway, enlarged, partially exploded plan view drawing of the components of a carpule approach to hypodermic syringes according to the present invention in a fourth embodiment.

DESCRIPTION OF THE PREFERRED EMBODIMENTS:

A first approach to solving the problem is depicted in FIGS. 5–11. As with all the embodiments to be described hereinafter, the carpule 10 remains the same. The two-ended needle assembly 12′ is substantially the same as the two-ended needle assembly 12 of the prior art with a few notable exceptions which can be implemented by merely changing the shape of the molds in which the plastic portions are formed. For one, the concentrically-located center piece 46 extending from the cap 21 and carrying the needle 22 is somewhat extended in length. It has a locking ridge 48 (to be described in greater detail shortly) circumferentially formed in the outer surface thereof. It also has a groove 50 formed therein to create a weak point. The two-ended needle assembly 12′ is shipped with a cover 28 in the usual manner.

Use of the two-ended needle assembly 12′ begins in the same way as with the prior art two-ended needle assembly 12 as described above. With the cover 28 in place and the cap 21 positioned on the closed end of the carpule 10, the carpule is inserted into the syringe assembly 30 with the needle 22 and cover 28 through the hole 32. The knob 36 is then tightened to secure the carpule 10 in place and pierce its end with the carpule-piercing tip 26. The cover 28 is then removed, which is not a problem since the needle 22 is still unused. As depicted in FIGS. 5 and 9, the protective sleeve assembly 52 is shipped in a hard cover 34. The protective sleeve assembly 52 comprises a base portion 56 having a socket 58 therein communicating with a concentric bore 60. The socket 58 is shaped to receive the center piece 46. The slats 62 of a Kuracina type protective sleeve 64 extend outward from the base portion 56 around the bore 60. In the usual way, the slats 62 terminate in an end-piece 66 and a spring 68 and locking collar 70 are positioned over the slats 62.

As depicted in FIG. 9, the protective sleeve assembly 52 is placed over the needle 22 and snapped in place using the hard cover 54. The locking ridge 48 snaps into a mating locking groove 72. As can be seen in the drawings, both the locking ridge 48 and the mating locking groove 72 are sawtooth-shaped. Thus, once they are snapped together, they are locked together and cannot be easily separated again. The hard cover 54 is then removed as depicted in FIG. 10 and the syringe assembly 30 is ready for use in combination with the protective sleeve assembly 52 in its usual manner.

As can be seen and appreciated from the drawing figures, once the protective sleeve assembly 52 has been attached to the center piece 46, the protective sleeve assembly 52 cannot be withdrawn back through the hole 32 if, in fact, it is a bore through the end of the syringe assembly 30. If the "hole" 32 is actually a slot open at the top, it may be possible to lift the two-ended needle assembly 12′ and protective sleeve assembly 52 out of the hole 32 and dispose of them in combination. Not knowing what type of syringe assembly 30 will be employed, however, this embodiment of the present invention provides for either configuration. If the two-ended needle assembly 12′ and protective sleeve assembly 52 are on opposite sides of a bore, the hard cover 54 is replaced over the protective sleeve assembly 52 and then used to break the center piece 46 and needle 22 off at the weak point created by the groove 50 mentioned above and as depicted in FIG. 11. Some body fluids may be present at the points of breakage of the needle 22; but, there should be no sharp points extending to create a needle-stick problem if the hard cover 54 containing the protective sleeve assembly 52 and needle 22 is handled with care and gloved hands.

A somewhat similar approach which does not require the breaking off of the needle is depicted in FIGS. 12–17. In this embodiment, the two-ended needle assembly is replaced by a piercing cap 74 carrying the carpule-piercing tip 26 portion of a needle communicating with a concentric needle-receiving bore 76. As depicted in FIGS. 12 and 14, the protective sleeve assembly 52 is of identical construction to the previous embodiment and the needle as carried by a plastic piece 78 shaped to snap-fit into the socket 58 is shipped in the socket 58 and covered by the hard cover 54. The needle 22 could also be fixed within the protective sleeve assembly 52 in other ways known to those skilled in the art and its method of attachment is not a point of novelty of this embodiment. An untipped mounting portion 80 of a length substantially equal to that of the needle-receiving bore 76 extends from the bottom surface of the protective sleeve assembly 52. After the piercing cap 74 has been placed on the carpule 10 and the two locked into the syringe assembly 10 as depicted in FIG. 13, the assembled needle 22 and protective sleeve assembly 52 with hard cover 54 in place are mounted to the syringe assembly 30 by inserting the mounting portion 80 into the needle-receiving bore 76 as depicted in FIG. 15. The hard cover 54 is then removed as depicted in FIG. 16 and the syringe assembly 30 is ready for use in combination with the protective sleeve assembly 52. After use, the hard cover 54 is replaced and the protective sleeve assembly 52 is removed by withdrawing the mounting portion 80 from the needle-receiving bore 76 as depicted in FIG. 17. The mounting portion 80 of the needle 22 is exposed in this embodiment and may have bodily fluids emerging therefrom; but, it is not sharp and, therefore, the chance of needle-stick from the blunt end is minimal if care is taken in handling.

A third embodiment of the present invention is shown in FIGS. 18 and 19. In this case, the carpule 10 has a cylindrical cap-guide 82 placed over its closed end before it is inserted into the syringe assembly 30 and tightened in place with the knob 36. The cap-guide 82 merely provides an extended support tube 84 through the hole 32. The protective sleeve assembly 52 is formed as part of a modified two-ended needle assembly 88. In the modified two-ended needle assembly 88, the cap 21′ is sized to fit over the support tube 84 instead of the collar 20 of the carpule 10. Also, the carpule-piercing tip 26 is extended in length so as to reach and pierce the end of the carpule 10 through the support tube 84 when the cap 21′ is fit over the support tube 84 as depicted in FIG. 19. Note also that for added protection, the carpule-piercing tip 26 is disposed within a protective tube 86. The protective tube 86 bears against the end of the carpule 10 and retracts as the cap 21′ is fit over the support tube 84 as depicted in FIG. 19. It then extends to cover the carpule-piercing tip 26 when the carpule-piercing tip 26 is withdrawn. For best operation in this regard, it is preferred that the protective tube 86 be slit longitudinally to create slats so that it operates in the manner of the protective sleeve assembly 52. This embodiment offers the additional benefit of more securely supporting the needle 22 and the protective sleeve assembly 52 on the syringe assembly 30 in use.

Figure 21:
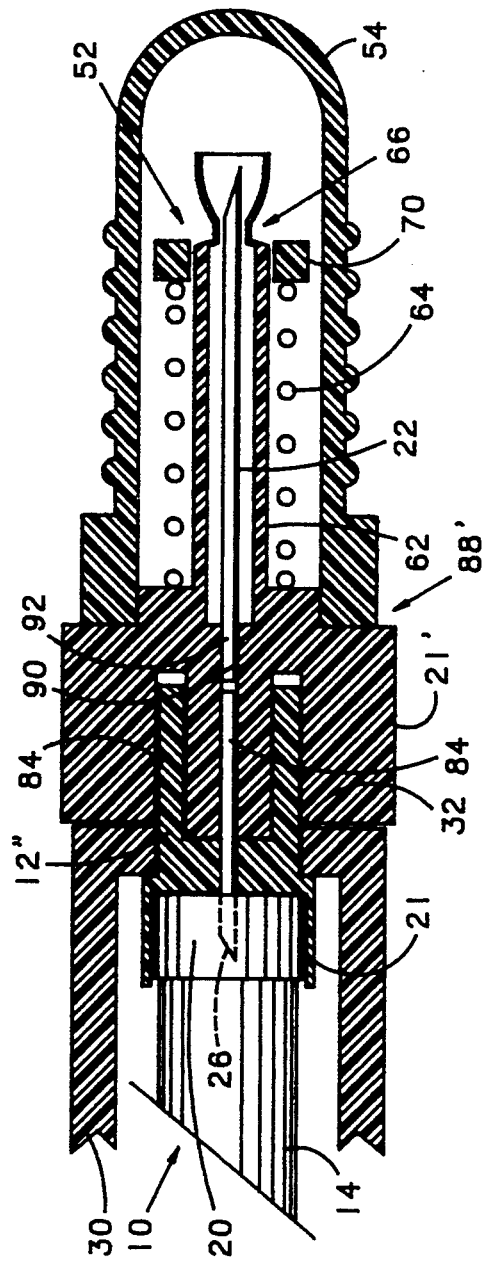
FIG. 21 is a partially cutaway, enlarged, plan view drawing of the components of a carpule approach to hypodermic syringes according to the present invention in its fourth embodiment of FIG. 20 shown fully assembled for use.

A fourth and preferred embodiment is depicted in FIGS. 20 and 21. This embodiment is preferred because it provides the support for the needle 22 and the protective sleeve assembly 52 on the syringe assembly 30 in use of the last-described embodiment while having no exposed portions of the needle 22 after use. There is a modified two-ended needle assembly 12″ having the usual cap 21 sized to fit over the collar 20 of the carpule 10 and a carpule-piercing tip 26 for piercing the end of the carpule 10. As in the previous embodiment, there is a support tube 84 extending from the cap 21 concentric with the carpule-piercing tip 26 and extending through the hole 32. Also, the out portion of the carpule-piercing tip 26 is extended along the length of the support tube 84 as depicted in the drawing figures. Also similar to the last-described embodiment, the protective sleeve assembly 52 is formed as part of a modified two-ended needle assembly 88′ in which the cap 21′ is sized to fit over the support tube 84. Rather than the carpule-piercing end of the needle 22 extending out from the cap 21′, however, the end terminates in a needle-receiving bore 90 contained within a cylindrical tube 92 extending concentrically from the inside of the cap 21′. Thus, when the components are fit together for use as depicted in FIG. 21, the tube 92 and the support tube 84 intermesh internally and externally with the extended portion of the carpule-piercing tip 26 disposed within the needle-receiving bore 90 so as to provide a firm attachment of the needle 22 and protective sleeve assembly 52 on the syringe assembly 30 in use.

It should be noted with particularity with respect to both these two latter-described embodiments that the interlocking components need not be cylindrical in shape and, in fact, a non-cylindrical shape can be employed for alignment purposes as illustrated in FIGS. 22a–b. If, for example, the tube 92 and the support tube 84 of the last-described embodiment are made triangular in cross-sectional shape and the bevel of the injection tip 24 of the needle 22 is positioned in a pre-established way with respect to the sides of the triangular cross sections, the bevel of the injection tip 24 of the needle 22 can be positioned in a known way for use as the components are assembled in the syringe assembly 30.

Wherefore, having thus described the present invention,

What is claimed is:

1. In a carpule-using syringe assembly wherein a syringe assembly carries a carpule for piercing by a needle also carried by the syringe assembly, the improvement for adding a protective sleeve to the needle comprising:

a) a cap disposed over a pierceable end of the carpule, said cap having a support portion extending concentrically outward therefrom and extend beyond an outer end of the syringe assembly, said support portion having a longitudinal bore therethrough; and, b) a protected needle assembly carried by said support portion, said protected needle assembly including the needle with an inner portion disposed in said bore and a retractable protective sleeve disposed over an outer tip portion of the needle; wherein, c) the needle is in two parts comprising a carpule-piercing part and a patient piercing part;

d) said bore comprises an inner bore adjacent said cap on one end carrying an inner portion of said carpule-piercing part and an outer bore of larger diameter than said inner bore on an opposite end concentrically extending over an outer portion of said carpule-piercing part; and, e) said retractable protective sleeve is carried by a base member also carrying said patient piercing part of the needle in a central bore therethrough, said base member having a projection extending therefrom containing a portion of said central bore not carrying said patient piercing part, said projection being sized and shaped to fit within said outer bore with said outer portion of said carpule-piercing part disposed within said portion of said central bore not carrying said patient piercing part.

2. The improvement to a carpule-using syringe assembly for adding a protective sleeve to the needle thereof of claim 1 wherein additionally:

said projection is concentrically disposed in an outer bore of said base member sized and shaped to fit over said opposite end of said support portion.

3. The improvement to a carpule-using syringe assembly for adding a protective sleeve to the needle thereof of claim 1 wherein:

mating portions of said cap and said protected needle assembly are non-cylindrical and of mating cross-sectional shapes having a pre-established relationship to a positional orientation of a patient-piercing tip of the needle whereby the positional orientation of said patient-piercing tip can be established when the syringe assembly is assembled with the carpule and said protected needle assembly.

4. A carpule-using syringe assembly having a needle protected to minimize the chance of accidental needle-stick comprising:

a) a carpule having a pierceable end;

b) syringe body means for receiving and holding said carpule with said pierceable end adjacent an opening in an end portion of said syringe body means;

c) a cap disposed over said pierceable end, said cap including support means disposed in said opening;

d) carpule-piercing means for piercing said pierceable end of said carpule through said cap;

e) a needle having a patient-piercing end;

f) a retractable protective sleeve comprising a plurality of longitudinal slats disposed over said patient-piercing end of said needle; and, g) means for attaching said needle and said retractable protective sleeve in combination to said support means with said needle in communication with an interior portion of said carpule through said carpule-piercing means.

* * * * *